United States Patent
Lele et al.

(10) Patent No.: US 10,515,450 B2
(45) Date of Patent: Dec. 24, 2019

(54) SYSTEMS AND METHODS FOR USING A SINGLE-CELL TO CREATE CHROMOSOMAL SPREADS

(71) Applicant: University of Florida Research Foundation, Inc., Gainesville, FL (US)

(72) Inventors: Tanmay P. Lele, Alachua, FL (US); Wallace Gregory Sawyer, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 35 days.

(21) Appl. No.: 15/789,414

(22) Filed: Oct. 20, 2017

(65) Prior Publication Data

US 2018/0114316 A1 Apr. 26, 2018
US 2019/0073766 A2 Mar. 7, 2019

Related U.S. Application Data

(60) Provisional application No. 62/410,553, filed on Oct. 20, 2016.

(51) Int. Cl.
| | | |
|---|---|---|
| *G06T 7/00* | (2017.01) |
| *G01N 33/50* | (2006.01) |
| *B01L 3/00* | (2006.01) |
| *C12Q 1/6851* | (2018.01) |
| *C40B 40/06* | (2006.01) |

(52) U.S. Cl.
CPC ........ *G06T 7/0012* (2013.01); *B01L 3/50273* (2013.01); *C12Q 1/6851* (2013.01); *C40B 40/06* (2013.01); *G01N 33/50* (2013.01); *B01L 2400/0481* (2013.01)

(58) Field of Classification Search
None
See application file for complete search history.

(56) References Cited

U.S. PATENT DOCUMENTS

| | | | |
|---|---|---|---|
| 9,133,506 B2* | 9/2015 | Katzir | ................ G06K 9/00134 |
| 2009/0048785 A1* | 2/2009 | Katzir | .................. C12Q 1/6841 702/20 |
| 2015/0010617 A1* | 1/2015 | Shaaltiel | .................. C12N 9/22 424/450 |
| 2018/0114316 A1* | 4/2018 | Lele | ........................ C40B 40/06 |

OTHER PUBLICATIONS

Paul Grayson, Lin Han, Tabita Winther, and Rob Phillips, "Real-time observations of single bacteriophage λ DNA ejections in vitro", PNAS Sep. 11, 2007 104 (37) 14652-14657; https://doi.org/10.1073/pnas.0703274104. (Year: 2007).*

* cited by examiner

*Primary Examiner* — Tahmina N Ansari
(74) *Attorney, Agent, or Firm* — Thomas|Horstemeyer, LLP

(57) ABSTRACT

Embodiments of the present disclosure provide for methods and systems for preparing chromosomal spread for a selected cell so that chromosomal spreads and/or translocations can be correlated with the selected cell.

12 Claims, 3 Drawing Sheets

SYSTEMS AND METHODS FOR USING A SINGLE-CELL TO CREATE CHROMOSOMAL SPREADS

CROSS-REFERENCE TO RELATED APPLICATIONS

This application claims benefit of U.S. Provisional Application No. 62/410,553, filed Oct. 20, 2016, which is hereby incorporated herein by reference in its entirety.

BACKGROUND

The shape and size of the nucleus is an important prognostic marker for diseases. In particular, the shape and size of the nucleus in a cell can be used to identify a number of different types of cancers. However, the mechanisms by which the cancer nucleus becomes abnormal in shape are poorly understood. One potential mechanism is that altered number of chromosomes and/or chromosomal translocations contribute to abnormal cancer nuclear shapes.

Currently, methods that can be used to prepare chromosomal spreads rely on colliding a drop containing many cells (e.g., millions of mitotic cells (cells lacking a nucleus)) against a surface to spread out the DNA. The disadvantage of this method is that it is not possible to map a given chromosomal spread to an image of the nucleus that housed it, nor the cell. This makes it difficult to correlate chromosomal spreads and/or translocations with cell and nuclear phenotype.

SUMMARY

Disclosed herein is a method for assaying chromosomal content in a cell containing a nucleus. The method involves imaging the cell first, then applying downward compression on the cell in a manner sufficient to eject DNA out of the cell; and then imaging the ejected DNA. In some embodiments, the cells are adherent and mitotic, and could include any of the cell types in the human body. In other embodiments, cells could be in suspension, such as cancer stem cells or part of tissue such as myotubes, endothelium or cardiovascular tissue. In particular embodiments, the cell is a cancer cell. Alternatively, it could be a cell from patients with progeria, cell from muscular dystrophy, laminopathy or lipodystrophy patients, or it could be a cell from aging humans.

Vertical downward compression can be applied using any means suitable to compress and rupture the cell in a controlled manner. For example, the compression can be applied using a glass slide or slide of other material, cantilever, sphere, or cylinder (rod) made of glass or other material. In particular embodiments, the cell is compressed with a rod using downward/vertical pressure. In some cases, the rod is also actuated in a horizontal plane to apply shear in addition to compression. Compression and/or shear can also be applied using fluid flow, such as jet flow or hydrostatic pressure. Alternatively, cells may be extruded under pressure through narrow pores to burst the nucleus and remove chromosomal contents.

In some embodiments, the compression involves a single downward force at a speed and force sufficient to eject the DNA. In other embodiments, the compression involves oscillating vertical and tangential forces at controlled frequencies, with or without fluid flow.

In order for ejected DNA to adequately spread, compression is preferably accompanied by a horizontal force. In some embodiments, this horizontal force is achieved by the force of ejection. This force can be increased by, for example, increasing intracellular/intranuclear pressure prior to compression. In particular embodiments, the method involves osmotically swelling the cell prior to compression to increase DNA ejection. For example, in some embodiments, the cells are arrested (e.g. the combined treatment of thymidine and nocodazole) and fixed at the pro-metaphase/metaphase. The culture media can then be replaced, for example, with a hypotonic solution (e.g. 0.56% KCl solution) to induce osmotic imbalance for cell/nucleus swelling. The consequentially increased hydrostatic pressure inside these inflated cell, which is balanced by the cellular/nuclear membrane tension, can enhance the horizontal DNA ejection once the membranes are disrupted either by the vertical compression of microprobe In some embodiments, the method involves applying horizontal flow during compression to increase spread of the ejected DNA. This flow can also be used to transfer the ejected DNA after imaging for further analysis.

The disclosed method can further involve quantifying chromosomal content from the ejected DNA. For example, images of the DNA can be used to identify chromosomal duplications, deletions, or rearrangements. DNA can be collected, and labeled with chromosome specific probes that allow identification of chromosomes. Specific genes could be labeled to determine their position on chromosomes, and this information correlated with nuclear and cell phenotype before compression.

The disclosed method involves imaging the cell prior to compression. For example, the nucleus becomes abnormally shaped in a large number of cancers, and its appearance can be a diagnostic metric. Imaging can be done after fluorescently labeling specific targets in the cell using immunolabeling, expressing proteins conjugated with fluorescent dyes or green fluorescent protein, or using quantum dots to recognize proteins, confocal fluorescence or other fluorescence imaging methods (epifluorescence, super-resolution microscopy) can be used to image cells. Images collected can be used, for example, to measure cell volume, nuclear volume, cell shape, nuclear shape, nuclear invaginations, or any combination thereof. Images can also be used to detect organization of the cytoskeleton and/or to detect localization of the mitochondria, ER and golgi body and similar such cell biological organelles. Images can be used to measure mitochondrial activity in the cell prior to compression. Images can be used to quantify localization of chosen proteins like transcription factors in specific locations of the cell and or fluorescence methods like photobleaching, FRET or other methods can be used to quantify protein interactions or protein dynamics.

One advantage of the disclosed methods is the ability to correlate observations of these types with chromosomal content. Quantifying chromosomal abnormalities simultaneously with cellular parameters like nuclear volume and shape, protein dynamics, protein interactions, localization of proteins, size and localization of other organelles like ER, golgi or mitochondria, and cellular geometry may improve diagnostic outcomes. For example, the nucleus can be abnormally shaped in a certain cancer, without changes to chromosomal content. While chromosomal duplications, deletions or rearrangements might occur in other cancers and cause abnormal cellular parameters. Collecting such information about cancers can improve diagnose and treatment of cancers. Nuclear abnormalities also occur in human aging, and therefore combining chromosomal spreads with nuclear shape measurements in aging populations can help understand how to 'normalize' aged cell populations. Such abnormalities also occur in a host of other diseases like progeria, laminopathies, lipodystrophies, muscular dystrophies and cardiomyopathies.

In some embodiments, the disclosed method can be used to select a suitable therapeutic, e.g. based on the chromosomal content and/or its relationship to other observations of the cell prior to compression. For example, if chromosomal abnormalities are determined to be not responsible for nuclear volume and shape changes in a pathological state, this may suggest a different target for nuclear abnormalities and a different treatment modality as compared to if chromosomal abnormalities are observed. Similarly, if chromosomal abnormalities are found to correlate with mitochondrial abnormalities or abnormal localization of proteins to the ER or golgi, or with changes in cell volume, this information can help develop better target for therapies.

Also disclosed is a device for processing cells that includes a stage configured to hold a container or slide comprising a cell, an imaging apparatus configured to acquire an image at a plurality of locations in a scan area of the container or slide, and a compression apparatus configured to apply vertical pressure on the cell in a manner sufficient to eject DNA from the cell.

In some embodiments, the compression apparatus involves a rod (e.g. glass rod) positioned over the scan area.

In some embodiments, the compression apparatus involves a fluidic apparatus configured to apply compression flow on the cell, configured to apply horizontal shear flow on the cell in a manner sufficient to increase spread of the ejected DNA, or a combination thereof.

In some embodiments, the device also includes a computer program on computer readable medium with instructions to cause the device to carry out a method that involves imaging a first cell at a first location in the scan area, applying downward compression using the compression apparatus in an manner sufficient to eject DNA out of the cell, and imaging the ejected DNA. In some cases, the instructions further cause the device to repeat these steps on a second cell at a second location in the scan area.

The imaging apparatus can also contain an image processor operable to process the image to identify and select a cell in a scan area for processing by the method. The computer readable medium can also include instructions to process the image of the cell to measure one or more of cell volume, nuclear volume, cell shape, nuclear shape, and nuclear invaginations. The computer readable medium can also comprises instructions to process the image of the ejected DNA to detect chromosomal content.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
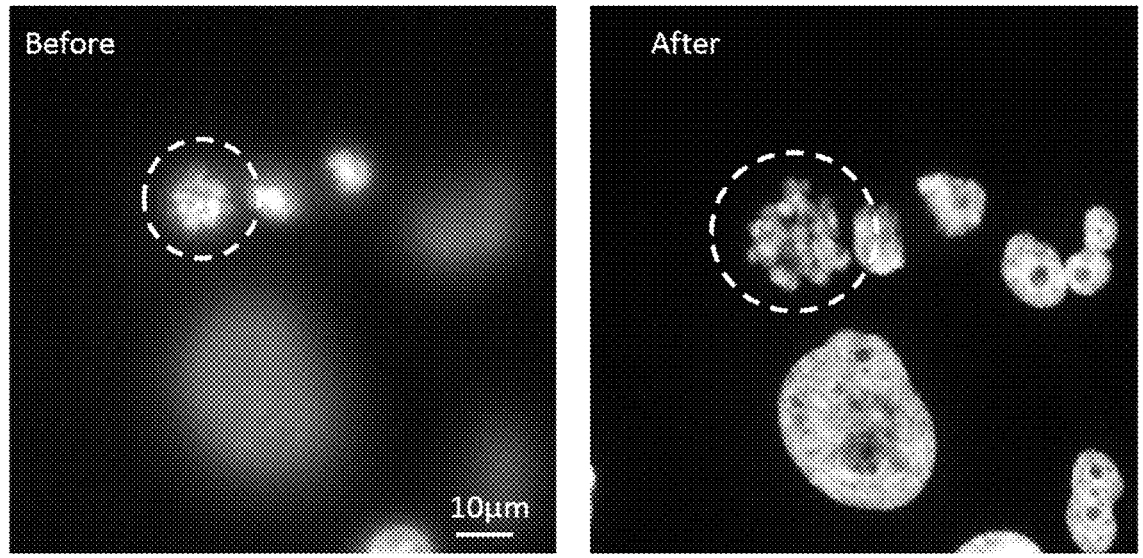
FIGS. 1 to 3 are images of non-swelled cells before and after being compressed to cause chromosomal spreading.

Embodiments of the present disclosure provide for methods and systems for preparing chromosomal spread for a selected cell so that chromosomal spreads and/or translocations can be correlated with the selected cell. In an embodiment, systems and methods can be used to prepare chromosomal spreads that can be correlated with the shape of the nucleus before mitosis. In an embodiment, a cell can be selected and imaged using an imaging technique (e.g., a microscope) and then a shear and/or a compression force can be applied to the selected cell and the chromosomal spread can be imaged. Once a chromosomal spread is created from the selected cell and imaged and analyzed using the imaging system, a fluidic system can be used to transfer the chromosomal spread for additional analysis. In an embodiment, shear and compression forces can be applied to mitotic, adherent cells, to obtain the chromosomal spread of the selected cell. In this regard, embodiments of the present disclosure can be used to map the chromosomal content and chromosomal translocations onto nuclear and cell shapes and cell content (e.g., pre-mitotic nuclear and cell shapes and nuclear and cell content) for a single selected cell.

In an embodiment, the compression can be performed by moving a blunt vertical structure (e.g., a glass slide or a cylinder) into a substrate (e.g., a dish) with cultured cells arrested in mitosis between the structure and the substrate. The substrate can be imaged from the bottom with a 60× objective on a Nikon epifluorescence microscope, for example, before and after application of the compression and/or shear forces. The cylinder is first centered in the field of view. By compressing down with the cylinder on top of cell while observing cell simultaneously on the microscope, it is possible to image chromosomes before and after compression of the optionally osmotically swelled cell. In an embodiment, the substrate can include a fluidic or microfluidic channel that can include the selected cell or the substrate can be in fluidic communication with the chromosomal spread, so that the chromosomal spread can be flowed from the substrate and further analyzed. In an embodiment, the fluidic system can be used to flow a fluid before and/or during compression, which may further enhance chromosomal spreading by applying another shearing force. In an embodiment, the substrate can be part of a fluidic system that can be interfaced with an analysis system.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Figure 2:
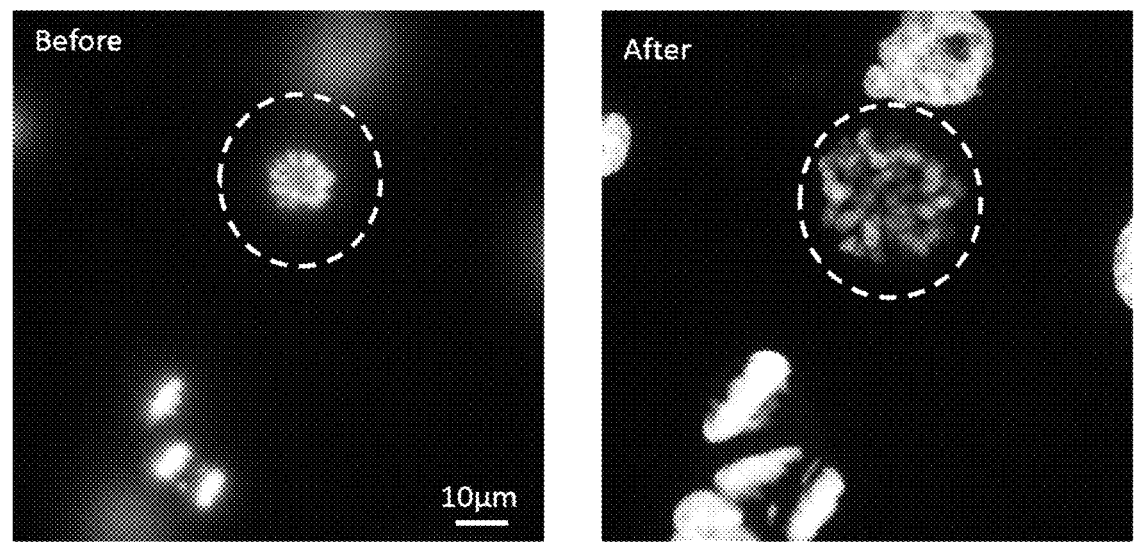
Figure 3:
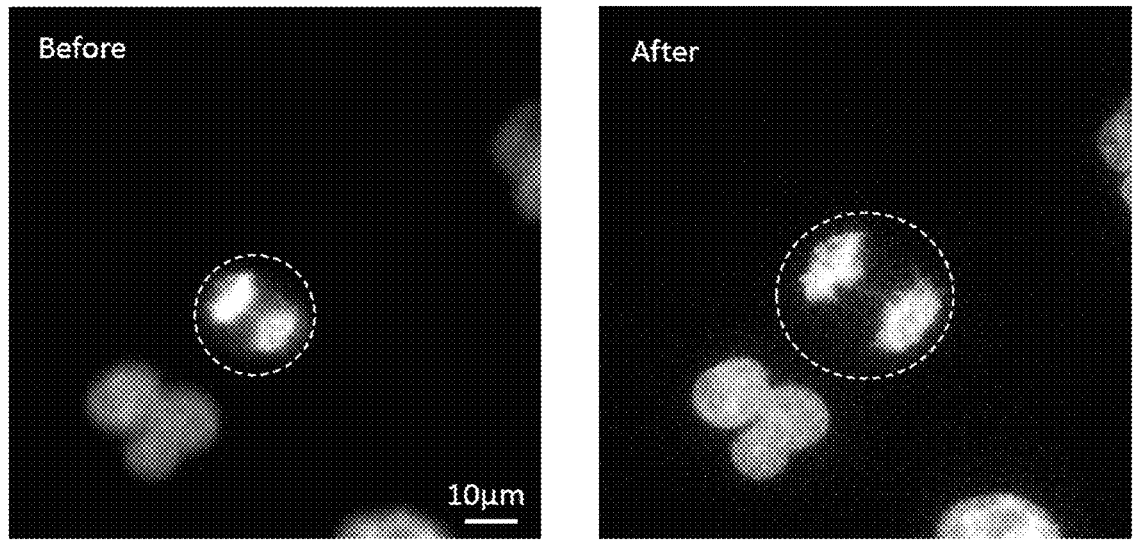
Figure 4:
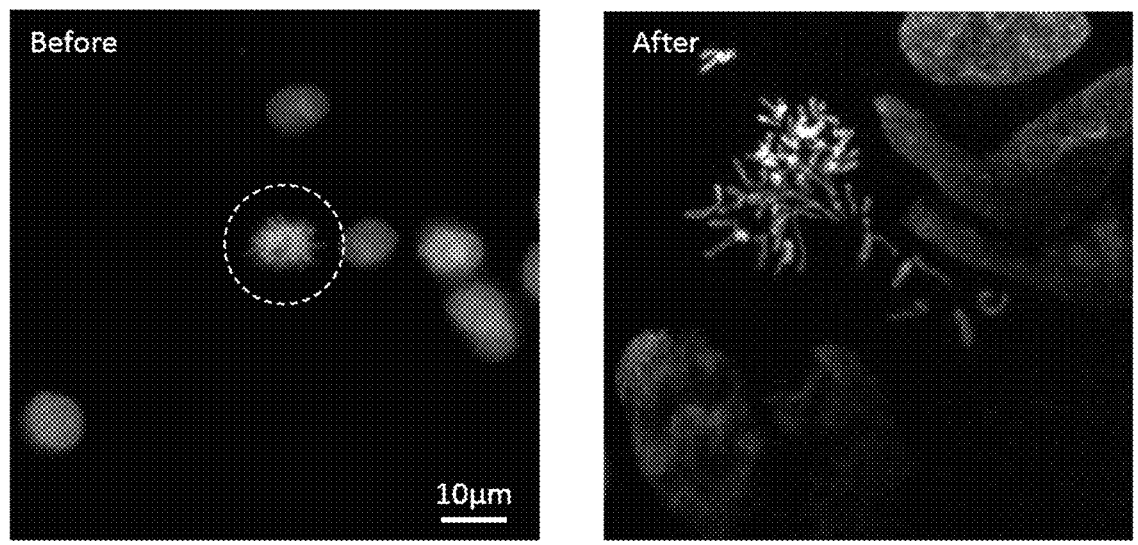
FIGS. 4 to 6 are images of swelled cells before and after being compressed to cause chromosomal spreading
Figure 5:
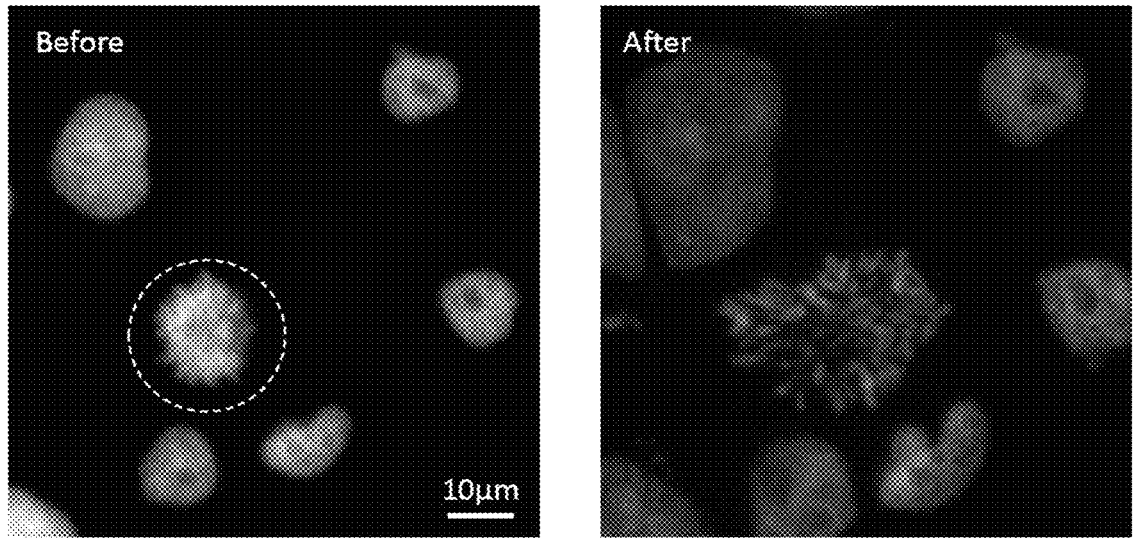
Figure 6:
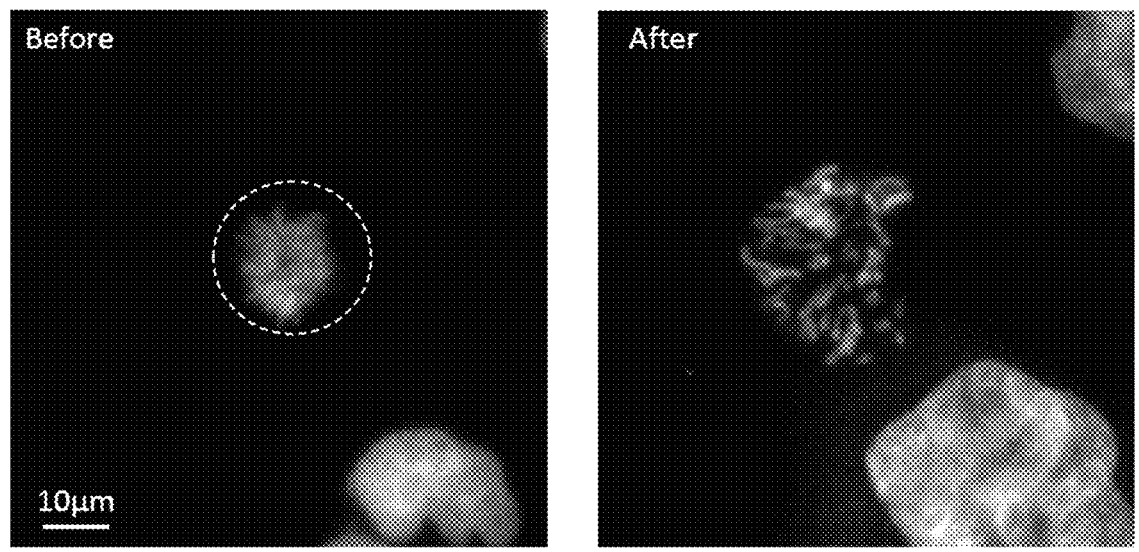

FIGS. 1 to 6 illustrate the spread chromosomes in unswelled and osmotically swollen (e.g., with water or other fluid that osmotically swells) cells. In an embodiment, the method and system include both the use of hydrodynamic shear and compression to generate the chromosomal spread of a selected cell.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for assaying a plurality of nucleated cells, comprising
   (a) imaging a first cell at a first location in a scan area;
   (b) applying downward compression on the first cell in an manner sufficient to eject DNA out of the first cell into the scan area;
   (c) imaging the ejected DNA;
   (d) repeat steps (a) to (c) on a second cell at a second location in the scan area.

2. The method of claim 1, wherein the vertical downward compression is applied using a vertical rod.

3. The method of claim 1, wherein the vertical downward compression is applied using jet flow.

4. The method of claim 1, further comprising quantifying chromosomal content from the ejected DNA.

5. The method of claim 1, further comprising measuring mitochondrial activity in the cell prior to step (b).

6. The method of claim 1, wherein step (a) comprises measuring cell volume, nuclear volume, or a combination thereof.

7. The method of claim 1, wherein step (a) comprises measuring cell shape, nuclear shape, nuclear invaginations, or any combination thereof.

8. The method of claim 1, wherein step (a) comprises detecting organization of the cytoskeleton, and ER and golgi body localization.

9. The method of claim 1, wherein the cell is a cancer cell.

10. The method of claim 1, further comprising selecting a suitable therapeutic based on the chromosomal content.

11. The method of claim 1, further comprising osmotically swelling the cell prior to step (b).

12. The method of claim 1, wherein step (b) further comprises applying horizontal shear on the cell to increase spread of the ejected DNA.

* * * * *